(12) United States Patent
Aloise

(10) Patent No.: US 10,716,645 B2
(45) Date of Patent: Jul. 21, 2020

(54) VARIABLE HEAT-TREAT ENDODONTIC FILE

(71) Applicant: Ormco Corporation, Orange, CA (US)

(72) Inventor: Carlos A. Aloise, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 102 days.

(21) Appl. No.: 15/789,130

(22) Filed: Oct. 20, 2017

(65) Prior Publication Data

US 2018/0110588 A1 Apr. 26, 2018

Related U.S. Application Data

(60) Provisional application No. 62/411,603, filed on Oct. 22, 2016.

(51) Int. Cl.
| | |
|---|---|
| *A61C 5/42* | (2017.01) |
| *C22C 19/00* | (2006.01) |
| *C22F 1/00* | (2006.01) |
| *A61B 17/16* | (2006.01) |
| *B24B 19/04* | (2006.01) |

(52) U.S. Cl.
CPC .............. *A61C 5/42* (2017.02); *C22C 19/007* (2013.01); *C22F 1/006* (2013.01); *A61B 17/1615* (2013.01); *A61C 2201/007* (2013.01); *B24B 19/04* (2013.01)

(58) Field of Classification Search
CPC . A61C 5/42; A61C 2201/007; A61B 17/1615; C22C 19/007; C22F 1/006; B24B 19/04
USPC ........................................................ 433/102
See application file for complete search history.

(56) References Cited

U.S. PATENT DOCUMENTS

| | | |
|---|---|---|
| 1,022,838 A | 4/1912 | Funk |
| 4,457,710 A | 7/1984 | McSpadden |
| 4,889,487 A | 12/1989 | Lovaas |
| 4,904,185 A | 2/1990 | McSpadden |
| 5,104,316 A | 4/1992 | McSpadden |
| 5,464,362 A | 11/1995 | Heath et al. |
| 5,527,205 A | 6/1996 | Heath et al. |
| 5,628,674 A | 5/1997 | Heath et al. |
| 5,655,950 A | 8/1997 | Heath et al. |
| 5,762,541 A | 6/1998 | Heath et al. |
| 5,938,440 A | 8/1999 | McSpadden |
| 5,941,760 A | 8/1999 | Heath et al. |
| 5,984,679 A | 11/1999 | Farzin-Nia et al. |
| 6,149,501 A | 11/2000 | Farzin-Nia et al. |
| 6,315,558 B1 | 11/2001 | Farzin-Nia et al. |

(Continued)

FOREIGN PATENT DOCUMENTS

| | | |
|---|---|---|
| WO | WO2014/141241 | 9/2014 |
| WO | WO2018/105997 | 6/2018 |

OTHER PUBLICATIONS

Examination Report in Application No. 16202063.0, dated Jan. 31, 2019.

(Continued)

*Primary Examiner* — Matthew M Nelson
(74) *Attorney, Agent, or Firm* — Weiss & Arons LLP

(57) ABSTRACT

The present disclosure relates to the field of endodontic instrumentation, and more particularly to apparatus and methods for manufacturing that include applying a variable heat-treat to an endodontic file blank based on geometric parameters that will be formed in the blank.

10 Claims, 10 Drawing Sheets

(56) References Cited

U.S. PATENT DOCUMENTS

| | | | |
|---|---|---|---|
| 6,409,506 B1 | 6/2002 | Graybill | |
| 6,431,863 B1 | 8/2002 | Sachdeva et al. | |
| 6,783,438 B2 | 8/2004 | Aloise et al. | |
| RE39,174 E | 7/2006 | Buchanan | |
| 7,207,111 B2 | 4/2007 | Aloise et al. | |
| 7,270,541 B1 | 9/2007 | Johnson | |
| 7,300,281 B2 | 11/2007 | Cantatore et al. | |
| 7,435,086 B2 | 10/2008 | Berutti et al. | |
| 7,731,498 B2 | 6/2010 | McSpadden | |
| 7,766,657 B2 | 8/2010 | Jaunberzins | |
| 7,779,542 B2 * | 8/2010 | Aloise | B21F 99/00 148/563 |
| 7,967,605 B2 | 6/2011 | Goodis | |
| 8,062,033 B2 | 11/2011 | Luebke | |
| 8,182,265 B2 | 5/2012 | McSpadden | |
| 8,408,901 B2 | 4/2013 | Buchanan | |
| 8,562,341 B2 | 10/2013 | Luebke | |
| 8,714,976 B2 | 5/2014 | Johnson | |
| 8,727,773 B2 | 5/2014 | Luebke | |
| 8,876,991 B2 | 11/2014 | Luebke | |
| 8,911,573 B2 | 12/2014 | Heath et al. | |
| 8,916,009 B2 | 12/2014 | Ammon et al. | |
| 9,005,377 B2 | 4/2015 | Heath et al. | |
| 9,078,722 B2 | 7/2015 | Johnson | |
| 9,795,459 B2 | 10/2017 | Heath et al. | |
| 9,878,366 B2 | 1/2018 | Johnson | |
| 9,902,025 B2 | 2/2018 | Shotton et al. | |
| 9,931,179 B2 | 4/2018 | Rouiller | |
| 2002/0137008 A1 | 9/2002 | McSpadden et al. | |
| 2006/0014480 A1 * | 1/2006 | Aloise | B21F 99/00 451/149 |
| 2006/0068362 A1 | 3/2006 | Desrosiers et al. | |
| 2007/0137742 A1 | 6/2007 | Hao et al. | |
| 2008/0153055 A1 | 6/2008 | Senia et al. | |
| 2010/0003637 A1 | 1/2010 | Johnson | |
| 2010/0233648 A1 | 9/2010 | McSpadden et al. | |
| 2011/0159458 A1 * | 6/2011 | Heath | C22F 1/08 433/102 |
| 2011/0271529 A1 * | 11/2011 | Gao | A61C 5/42 29/896.1 |
| 2012/0219927 A1 | 8/2012 | Maxwell et al. | |
| 2012/0272526 A1 * | 11/2012 | Luebke | B21F 45/008 29/896.1 |
| 2013/0244200 A1 | 9/2013 | Rota et al. | |
| 2014/0004480 A1 | 1/2014 | Breguet | |
| 2014/0057226 A1 | 2/2014 | Buchanan | |
| 2015/0024342 A1 | 1/2015 | Jaunberzins | |
| 2015/0164614 A1 | 6/2015 | Shotton et al. | |
| 2015/0164615 A1 | 6/2015 | Shotton et al. | |
| 2015/0164617 A1 * | 6/2015 | Ammon | C22C 38/40 433/102 |
| 2016/0008092 A1 * | 1/2016 | Heath | C22F 1/10 148/563 |
| 2016/0256237 A1 | 9/2016 | Lee et al. | |
| 2017/0156818 A1 | 6/2017 | Aloise et al. | |
| 2017/0362694 A1 | 12/2017 | Luebke | |
| 2018/0008374 A1 | 1/2018 | Rota et al. | |
| 2018/0028280 A1 | 2/2018 | Scianamblo | |
| 2018/0036789 A1 * | 2/2018 | Luebke | A61C 5/40 |
| 2018/0049845 A1 | 2/2018 | McSpadden | |
| 2018/0085195 A1 | 3/2018 | Rouiller | |
| 2018/0110588 A1 | 4/2018 | Aloise | |
| 2018/0125609 A1 | 5/2018 | Malagnino | |
| 2018/0142377 A1 | 5/2018 | Gao et al. | |
| 2018/0177568 A1 | 6/2018 | Breguet et al. | |

OTHER PUBLICATIONS

Extended European Search Report in Application No. 17197635.0, dated Jun. 13, 2018.
"Ahead of the Curve: Using New Technology & Metallurgy to Address Endodontic Challenges," https://www.oralhealthgroup.com/features/ahead-of-the-curve-using-new-technology-metallurgy-to-address-endodontic-challenges/, May 1, 2014.
"Nickel Titanium," https://en.wikipedia.org/wiki/Nickel_titanium, Wikimedia Foundation, Inc., Retrieved on Sep. 30, 2016.
"R-Phase," https://en.wikipedia.org/w/index.php?title=R-Phase&printable=yes, Wikimedia Foundation, Inc., Retrieved on Oct. 5, 2016.
"Rotary Instrumentation: An Endodontic Perspective," American Association of Endodontics, Winter 2008.
Ashok Ayer, "Nickel Titanium in Endodontics," https://www.slideshare.net/ashokayer/nickel-titanium-in-endodontics, Aug. 31, 2014.
Santoro et al., "Pseudoelasticity and Thermoelasticity of Nickel-Titanium Alloys: A Clinically Oriented Review. Part I: Temperature Transitional Ranges," American Journal of Orthodontics and Dentofacial Orthopedics, vol. 119, No. 6, Jan. 2000.
Istvan Mihalcz, "Fundamental Characteristics and Design Method for Nickel-Titanium Shape Memory Alloy," https://pp.bme.hu/me/article/view/1410/814, Apr. 5, 2000.
Santoro et al., "Pseudoelasticity and Thermoelasticity of Nickel-Titanium Alloys: A Clinically Oriented Review. Part II: Deactivation Forces," American Journal of Orthodontics and Dentofacial Orthopedics, vol. 119, No. 6, Jun. 2001.
Kuhn et al., "Fatigue and Mechanical Properties of Nickel-Titanium Endodontic Instruments," https://www.jendodon.com/article/S0099-2399(05)60464-5/pdf, Journal of Endodontics, vol. 28, No. 10, Oct. 28, 2002.
Pelton et al., "The Physical Metallurgy of Nitinol for Medical Applications," https://link.springer.com/article/10.1007/s11837-003-0243-3, May 2003.
Carrotte, P., "Endodontics: Part 5 Basic Instruments and Materials for Root Canal Treatment," https://www.nature.com/articles/4811738, British Dental Journal, vol. 197 No. 8, Oct. 23, 2004.
Alapati, Satish B., "An Investigation of Phase Transformation Mechanisms for Nickel-Titanium Rotary Endodontic Instruments," https://www.researchgate.net/publication/267222080_an_investigation_of_phase_transformation_mechanism_for_nickel-titanium_rotary_endodontic_instruments, Ohio State University, 2006.
Zinelis et al., "The Effect of Thermal Treatment on the Resistance of Nickel-Titanium Rotary Files in Cyclic Fatigue," https://www.researchgate.net/publication/6399181_The_effect_of_thermal_treatment_on_the_resistance_of_nickel-titanium_rotary_files_in_cyclic_fatigue, Jun. 2007.
Drexel et al., "The Effects of Cold Work and Heat Treatment on the Properties of Nitinol Wire," https://www.asminternational.org/documents/10192/1849770/05219Z_Sample.pdf, ASM International, Sep. 23, 2007.
Gambarini et al., "Fatigue Resistance of Engine-Driven Rotary Nickel-Titanium Instruments Produced by New Manufacturing Methods," https://pdfs.semanticscholar.org/cc7c/e5241d820a12414783c9eca1bf4db3323393.pdf, Journal of Endodontics, vol. 34, No. 8, Aug. 2008.
Cunningham et al., "Effect of Temperature on Collage-Dissolving Ability of Sodium Hypochlorite Endodontic Irrigant," https://www.ncbi.nlm.nih.gov/pubmed/6928291, Journal of IMAB, 2009.
Liu, Jie, "Characterization of New Rotary Endodontic Instruments Fabricated from Special Thermomechanically Processed NiTi Wire," Ohio State University, 2009.
Dimitrov et al., "In Vitro Investigation of Influence of Temperature Rising On Periodontal Tissue During Endodontic Treatment," http://dx.doi.org/10.5272/jimab.1522009_32, Journal of IMAB-Annual Proceeding, Jun. 25, 2009.
Madureira et al., "Shaping Ability of Nickel-Titanium Rotary Instruments in Simulated S-Shpaed Root Canals," https://www.ncbi.nlm.nih.gov/pubmed/19969482, Dec. 6, 2009.
He et al., "Design Improvement and Failure Reduction of Endodontic Files through Finite Element Analysis: Application to V-Taper File Designs," https://www.sciencedirect.com/science/article/pii/S0099239910005054, Journal of Endodontics, vol. 36 No. 9, Sep. 2010.
Gutman et al., "Alteration in the Inherent Metallic and Surface Properties of Nickel-Titanium Root Canal Instruments to Enhance Performance, Durability and Safety: A focused Review," https://www.researchgate.net/publication/51628532_Alteration_in_the_

(56) References Cited

OTHER PUBLICATIONS

Inherent_Metallic_and_Surface_Properties_of_Nickel-_Titanium_Root_Canal_Instruments_to_Enhance_Performance_Durability_and_Safety_A_Focused_Review, International Endodontic Journal, Sep. 2011.
Rodrigues et al., "Influence of Different Manufacturing Methods on the Cyclic Fatigue of Rotary Nickel-Titanium Endodontic Instruments," https://www.researchgate.net/publication/51718582_Influence_of_Different_Manufacturing_Methods_on_the_Cyclic_Fatigue_of_Rotary_Nickel-Titanium_Endodontic_Instruments, Journal of Endodontics, vol. 37 No. 11, Nov. 2011.
Ruddle, Clifford J., "Endodontic Canal Preparation WaveOne Single-File Technique," https://www.endoruddle.com/tc2pdfs/126/WaveOne_Jan2012.pdf, Dentistry Today, Jan. 2012.
Ye, Jia, "Metallurgical Characterization of M-Wire Nickel-Titanium Shape Memory Alloy Used for Endodontic Rotary Instruments during Low-Cycle Fatigue," https://www.jendondon.com/article/S0099-2399(11)01153-8/pdf, Journal of Endodontics, vol. 38, No. 1, Jan. 2012.
Brantley et al., "Heat Treatment of Dental Alloys: A Review," http://dx.doi.org/10.5772/52398, INTECH, Sep. 19, 2012.
Alshehri, Mohammed, "Mechanical Endodontic Instrumentation," http://www.endoexperience.com/documents/RotationReciprocationorcombination.pdf, Available as of Oct. 21, 2012.
Shen et al., "Current Challenges and Concepts of the Thermomechanical Treatment of Nickel-Titanium Instruments," https://www.aae.org/specialty/wp-content/uploads/sites/2/2017/07/shenchallengesconceptsniti.pdf, Journal of Endodontics, vol. 39 No. 2 Feb. 2013.
"Vortex® Orifice Openers with M-Wire® NiTi," Dentsply Tulsa Dental Specialties, 2013.
Hemptinne et al., "In Vivo Intracanal Temperature Evolution During Endodontic Treatment After the Injection of Room Temperature or Preheated Sodium Hypochlorite," https://www.jendodon.com/article/S0099-2399(15)00138-7/pdf, Journal of Endodontics vol. 41, No. 7, Jul. 2015.
De Vasconcelos et al., "Evidence for Reduced Fatigue Resistance of Contemporary Rotary Instruments Expose to Body Temperature," https://escholarship.org/uc/item/4tx2j85v, May 1, 2016.
Lo Savio et al., "Influence of Heat-Treatment on Torsional Resistance to Fracture of Nickel-Titanium Endodontic Instruments," https://ac.els-cdn.com/S2452321616301755/1-s2.0-S2452321616301755-main.pdf?_tid=1abb724b-b328-46d1-a27c-b94ac4fb9ab3&acdnat=1547059241_327fdf7d535cad30d193flf334c5b4f, Jun. 20, 2016.
"Instruments Used in Endodontics," Retrieved on Sep. 5, 2017.
International Search Report in Application No. PCT/US2017/025854, dated Jul. 31, 2017.
Written Opinion in Application No. PCT/US2017/025854, dated Jul. 31, 2017.
Y. Yahata et al, International Endodontic Journal 42, 621-626: "Effect of Heat Treatment on Transformation Temperatures and Bending Properties of Nickel-Titanium Endodontic Instruments," Jun. 1, 2009.
Dr. Barbara Muller, "A Short History of the NiTi File Revolution," https://www.dental-tribune.com/clinical/a-short-history-of-the-niti-file-revolution/, May 24, 2016.
European Examination Report in Application No. 17197635.0, dated Feb. 12, 2020.

\* cited by examiner

Cross Section
At 3,8, And 12mm

FIG. 19

| SIZE | LENGTH | (A) TIP DIA. ±.010 | (B) TIP RADIUS ±.002" | (C) TIP HELIX ANGLE | (D) HELIX ANGLE AT 3 mm | (E) HELIX ANGLE AT 8 mm | (F) HELIX ANGLE AT 12 mm | (G) FLUTE DIA. AT TIP | (H) FLUTE DIA. AT 3 mm | (I) FLUTE DIA. AT 8 mm | (J) FLUTE DIA. AT 12 mm | (K) # OF FLUTES AT 3 mm | (L) # OF FLUTES AT 4 mm | (M) LENGTH OF FLUTES | (N) CROSS SECTION AT 3 mm | (O) CROSS SECTION AT 8 mm | (P) CROSS SECTION AT 12 mm |
|---|---|---|---|---|---|---|---|---|---|---|---|---|---|---|---|---|---|
| 06/.13 | 21 mm | .130 mm | .003" | 21°±2° | 20°±2° | 17°±2° | 17°±2° | .0062±.001 | .0131±.001 | .0216±.001 | .0294±.001 | 5 | NA | .629±.010 | .0141±.001 | .0215±.001 | .0300±.001 |
| 06/.13 | 25 mm | .130 mm | .003" | 21°±2° | 20°±2° | 17°±2° | 17°±2° | .0062±.001 | .0131±.001 | .0216±.001 | .0294±.001 | 5 | NA | .629±.010 | .0141±.001 | .0215±.001 | .0300±.001 |
| 06/.13 | 31 mm | .130 mm | .003" | 21°±2° | 20°±2° | 17°±2° | 17°±2° | .0062±.001 | .0131±.001 | .0216±.001 | .0294±.001 | 5 | NA | .629±.010 | .0141±.001 | .0215±.001 | .0300±.001 |
| 06/.18 | 21 mm | .180 mm | .003" | 25°±2° | 20°±2° | 16°±2° | 16°±2° | .0081±.001 | .0138±.001 | .0236±.001 | .0321±.001 | 4.5 | NA | .630±.010 | .0142±.001 | .0247±.001 | .0323±.001 |
| 06/.18 | 25 mm | .180 mm | .003" | 25°±2° | 20°±2° | 16°±2° | 16°±2° | .0081±.001 | .0138±.001 | .0236±.001 | .0321±.001 | 4.5 | NA | .630±.010 | .0142±.001 | .0247±.001 | .0323±.001 |
| 06/.18 | 31 mm | .180 mm | .003" | 25°±2° | 20°±2° | 16°±2° | 16°±2° | .0081±.001 | .0138±.001 | .0236±.001 | .0321±.001 | 4.5 | NA | .630±.010 | .0142±.001 | .0247±.001 | .0323±.001 |
| 06/.20 | 21 mm | .205 mm | .003" | 26°±2° | 21°±2° | 17°±2° | 16°±2° | .0108±.001 | .0152±.001 | .0253±.001 | .0321±.001 | 4 | NA | .630±.010 | .0144±.001 | .0248±.001 | .0307±.001 |
| 06/.20 | 25 mm | .205 mm | .003" | 26°±2° | 21°±2° | 17°±2° | 16°±2° | .0108±.001 | .0152±.001 | .0253±.001 | .0321±.001 | 4 | NA | .630±.010 | .0144±.001 | .0248±.001 | .0307±.001 |
| 06/.20 | 31 mm | .205 mm | .003" | 26°±2° | 21°±2° | 17°±2° | 16°±2° | .0108±.001 | .0152±.001 | .0253±.001 | .0321±.001 | 4 | NA | .630±.010 | .0144±.001 | .0248±.001 | .0307±.001 |

FIG. 20

| SIZE | LENGTH | (A) TIP DIA. ±.010 mm | (B) TIP RADIUS ±.002" | (C) TIP HELIX ANGLE ±2° | (D) HELIX ANGLE AT 3 mm ±2° | (E) HELIX ANGLE AT 8 mm ±2° | (F) HELIX ANGLE AT 12 mm ±2° | (G) FLUTE DIA. AT TIP ±.001 | (H) FLUTE DIA. AT 3 mm ±.001 | (I) FLUTE DIA. AT 8 mm ±.001 | (J) FLUTE DIA. AT 12 mm ±.001 | (K) # OF FLUTES AT 3 mm | (L) # OF FLUTES AT 4 mm | (M) LENGTH OF FLUTES ±.01 | (N) CROSS SECTION AT 3 mm ±.001 | (O) CROSS SECTION AT 8 mm ±.001 | (P) CROSS SECTION AT 12 mm ±.001 |
|---|---|---|---|---|---|---|---|---|---|---|---|---|---|---|---|---|---|
| 06/25 | 25 mm | .25 mm | .003" | 25° | 23° | 18° | 17° | .0110 | .0160 | .0270 | .0330 | 4 | NA | .630 | .0160 | .0270 | .0330 |
| 06/25 | 31 mm | .25 mm | .003" | 25° | 23° | 18° | 17° | .0110 | .0160 | .0270 | .0330 | 4 | NA | .630 | .0160 | .0270 | .0330 |
| 06/25 | 21 mm | .25 mm | .003" | 25° | 23° | 18° | 17° | .0110 | .0160 | .0270 | .0330 | 4 | NA | .630 | .0160 | .0270 | .0330 |
| 06/30 | 21 mm | .295 mm | .003" | 27° | 25° | 17° | 17° | .0125 | .0180 | .0285 | .035 | 3 | NA | .630 | .0180 | .0300 | .0350 |
| 06/30 | 25 mm | .295 mm | .003" | 27° | 25° | 17° | 17° | .0125 | .0180 | .0285 | .035 | 3 | NA | .630 | .0180 | .0300 | .0350 |
| 06/30 | 31 mm | .295 mm | .003" | 27° | 25° | 17° | 17° | .0125 | .0180 | .0285 | .035 | 3 | NA | .630 | .0180 | .0300 | .0350 |
| 06/35 | 21 mm | .32 mm | .003" | 26° | 23° | 16° | 16° | .0135 | .0180 | .0274 | .0324 | 3 | NA | .630 | .0190 | .0288 | .0337 |
| 06/35 | 25 mm | .32 mm | .003" | 26° | 23° | 16° | 16° | .0135 | .0180 | .0274 | .0324 | 3 | NA | .630 | .0190 | .0288 | .0337 |
| 06/35 | 31 mm | .32 mm | .003" | 26° | 23° | 16° | 16° | .0135 | .0180 | .0274 | .0324 | 3 | NA | .630 | .0190 | .0288 | .0337 |
| 06/40 | 21 mm | .39 mm | .003" | 27° | 22° | 19° | 18° | .0174 | .0214 | .0303 | .0360 | NA | 3 | .630 | .0220 | .0315 | .0375 |
| 06/40 | 25 mm | .39 mm | .003" | 27° | 22° | 19° | 18° | .0174 | .0214 | .0303 | .0360 | NA | 3 | .630 | .0220 | .0315 | .0375 |
| 06/40 | 31 mm | .39 mm | .003" | 27° | 22° | 19° | 18° | .0174 | .0214 | .0303 | .0360 | NA | 3 | .630 | .0220 | .0315 | .0375 |
| 06/45 | 21 mm | .44 mm | .003" | 27° | 21° | 17° | 16° | .0189 | .0220 | .0302 | .0348 | NA | 3 | .630 | .0241 | .0317 | .0353 |
| 06/45 | 25 mm | .44 mm | .003" | 27° | 21° | 17° | 16° | .0189 | .0220 | .0302 | .0348 | NA | 3 | .630 | .0241 | .0317 | .0353 |
| 06/45 | 31 mm | .44 mm | .003" | 27° | 21° | 17° | 16° | .0189 | .0220 | .0302 | .0348 | NA | 3 | .620 | .0241 | .0317 | .0353 |
| 06/50 | 21 mm | .470 mm | .003" | 27° | 22° | 17° | 17° | .0207 | .0234 | .0302 | .0360 | NA | 3 | .620 | .0246 | .0320 | .0369 |
| 06/50 | 25 mm | .470 mm | .003" | 27° | 22° | 17° | 17° | .0207 | .0234 | .0302 | .0360 | NA | 3 | .620 | .0246 | .0320 | .0369 |
| 06/50 | 31 mm | .470 mm | .003" | 27° | 22° | 17° | 17° | .0207 | .0234 | .0302 | .0360 | NA | 3 | .630 | .0246 | .0320 | .0369 |
| 06/55 | 21 mm | .54 mm | .003" | 26° | 21° | 17° | 17° | .0220 | .0241 | .0324 ±.0016 | .0367 ±.0016 | NA | 2 | .630 | .0260 ±.0016 | .0340 ±.0016 | .0375 ±.0016 |
| 06/55 | 25 mm | .54 mm | .003" | 26° | 21° | 17° | 17° | .0220 | .0241 | .0324 ±.0016 | .0367 ±.0016 | NA | 2 | .630 | .0260 ±.0016 | .0340 ±.0016 | .0375 ±.0016 |
| 06/55 | 31 mm | .54 mm | .003" | 26° | 21° | 17° | 17° | .0220 | .0241 | .0324 ±.0016 | .0367 ±.0016 | NA | 2 | .630 | .0260 ±.0016 | .0340 ±.0016 | .0375 ±.0016 |

VARIABLE HEAT-TREAT ENDODONTIC FILE

CROSS-REFERENCE TO RELATED APPLICATION

This application claims the benefit of U.S. Provisional Application No. 62/411,603, filed on Oct. 22, 2016, which is hereby incorporated by reference herein in its entirety.

FIELD OF TECHNOLOGY

The present invention relates to the field of endodontic instrumentation, and more particularly to rotary files used to clean, remove debris from, and/or shape a tooth's root canal during a dental procedure.

BACKGROUND

A tooth may develop a carious lesion. A carious lesion infects tooth tissue. A carious lesion infects tooth tissue in a root canal of the tooth. If tooth tissue in the root canal is infected, the infected tissue should be removed from the tooth to stop further spreading of the carious lesion and/or infection.

A dental procedure for removing infected tooth tissue from a root canal typically requires specialized tools. Such tools include an endodontic file. Endodontic files are typically used to remove infected tooth tissue from the root canal. Endodontic files are also used to remove infected tooth tissue from other parts of the tooth such as tissue adjacent to the root canal.

A shape of a root canal differs from patient to patient. Typically, the canal is narrow and tortuous. Root canal curvatures are typically divided in three categories: straight, moderate and severe. Endodontic files are flexible to navigate a curvature of the root canal.

Tables 1 and 2 (below) summarize averages of root canal configuration and lengths.

TABLE 1

Illustrative root canal configurations

| Tooth | Average Length | No. of roots | No. of canals |
|---|---|---|---|
| Maxillary anteriors | | | |
| Central incisor | 22.5 mm | 1 | 1 |
| Lateral incisor | 22.0 mm | 1 | 1 |
| Canine | 26.5 mm | 1 | 1 |
| Maxillary premolar | | | |
| First premolar | 20.6 mm | 2-3 | 1 (6%) |
| | | | 2 (95%) |
| | | | 3 (1%) |
| Second premolar | 21.5 mm | 1-3 | 1 (75%) |
| | | | 2 (24%) |
| | | | 3 (1%) |
| Maxillary molars | | | |
| First molar | 20.8 mm | 3 | 4 (93%) |
| | | | 3 (7%) |
| Second molar | 20.0 mm | 3 | 4 (37%) |
| | | | 3 (63%) |
| Third molar | 17.0 mm | 1-3 | |
| Mandibular anteriors | | | |
| Central incisor | 20.7 mm | 1 | 1 (58%) |
| | | | 2 (42%) |
| Lateral incisor | 20.7 mm | 1-2 | 1 (58%) |
| | | | 2 (42%) |
| Canine | 25.6 | 1 | 1 (94%) |
| | | | 2 (6%) |
| Mandibular molars | | | |
| First molar | 21.0 mm | 2-3 | 3 (67%) |
| | | | 4 (33%) |
| Second molar | 19.8 mm | 2 | 2 (13%) |
| | | | 3 (79%) |
| | | | 4 (8%) |
| Third molar | 18.5 mm | 1-2 | |

TABLE 2

Illustrative human teeth measurements

| Tooth | Length overall | Length of crown | Length of root |
|---|---|---|---|
| Maxillary anteriors | | | |
| Central incisor | 22.5 | 10 | 12 |
| Lateral incisor | 22 | 8.8 | 13 |
| Canine | 26.5 | 9.5 | 17.3 |
| Maxillary premolar | | | |
| First premolar | 20.6 | 8.2 | 12.4 |
| Second premolar | 21.5 | 7.5 | 14 |
| Maxillary molars | | | |
| First molar | 20.8 | 7.7 | 13.2 |
| Second molar | 20 | 7.2 | 13 |
| Third molar | 17.1 | 6.3 | 11.4 |
| Mandibular anteriors | | | |
| Central incisor | 20.7 | 8.8 | 11.8 |
| Lateral incisor | 21.1 | 9.6 | 12.7 |
| Canine | 25.6 | 10.3 | 15.3 |
| Mandibular premolar | | | |
| First premolar | 21.6 | 7.8 | 14 |
| Second premolar | 22.3 | 7.9 | 14.4 |
| Mandibular molars | | | |
| First molar | 21 | 7.7 | 13.2 |
| Second molar | 19.8 | 6.9 | 12.9 |
| Third molar | 15.8 | 6.7 | 11.8 |

Average of root canal length: 13.5

Endodontic files are described using the following nomenclature and associated equations:

$A$ = Tip $B$ = Taper $L1$ = length at 1 mm from the end of the file $L10$ = length at 10 mm from the end of the file $D1$ = file's diameter @$L1=A$(Tip)

$D10$ = file's diameter @$L10=B*10+(D1)$ $\beta$ = file's taper = $\text{TAN}-1(((D10/2)-(D1/2))/9)$ Endodontic files used to remove infected tissue from a root canal are small enough to remove infected tissue from the canal without damaging uninfected tooth tissue. Typical file lengths include 23 and 27 mm. Such lengths address short and long canals. Endodontic files are also tapered to "fit" into a root canal and reach an apical foramen of the canal. Some files may not be tapered. Table 3 below shows common file sizes.

TABLE 3

Common File Sizes
Common File Sizes measured in hundredths of a millimeter at the tip of the instrument (Do) (e.g., size 60, Do = 60/100 = 0.6 mm)

| 6 |
|---|
| 8 |
| 10 |
| 11 |
| 12 |
| 13 |
| 14 |
| 15 |
| 20 |
| 25 |
| 30 |
| 35 |
| 40 |
| 45 |
| 50 |
| 55 |
| 60 |
| 70 |
| 80 |
| 90 |
| 100 |
| 110 |
| 120 |
| 130 |
| 140 |

FIG. 1 shows illustrative taper designs and associated measurements.

Endodontic files may be rotated to remove infected tissue. The files are rotated by hand and/or machine. It is preferable to shape a canal in manner that, as close as possible, maintains the dimensions and/or proportionality of the original canal. Such a shaped canal reduces loss of strength in the surrounding tooth structure and allows the canal to later be filled during an obturation phase with as few voids as possible A desired apical size and taper includes shaping the canal into a conical or at least partially conical shape. The conical shape extends from an access cavity (at a coronal area of the tooth) to the apical foramen of the tooth. A conically shaped root canal facilitates removal of dentinal debris (e.g., necrotic tissue), and cleaning of the canal during an irrigation process of a dental procedure. The conical shape also facilitates proper flow of gutta-percha or other suitable sealants during a subsequent obturation phase of the root canal dental procedure.

However, because of their small size, endodontic files are susceptible to breaking during operation in the canal. For example, in operation, when navigating curved sections of the canal, a file is exposed to torsion and bending stresses. Such stresses are associated with a file breakage or other failures. Breakage of the file in the canal during the dental procedure is associated with undesirable complications. For example, it is difficult to extract a piece of the broken file from the canal.

Endodontic files are constructed from various materials, including stainless steel and Nickel Titanium ("NiTi"). NiTi is an alloy that typically exists in two crystal structures, austenite and martensite. NiTi also exists in a third crystal structure termed a rhombohedral phase or r-phase. A change between different NiTi crystal structures may be stress-induced or thermally induced. An ability of NiTi to transition from one crystal structure to the other provides NiTi files with superelastic and shape memory properties.

NiTi's superelasticity and high degree of flexibility make it an attractive choice for endodontic file fabrication. A highly elastic file remains centered in the root canal and has a lower propensity of canal straightening or other preparation errors. NiTi's shape memory provides an endodontic file with an ability to resist deformation in response to stresses applied to the file when operating in the canal.

Additionally, rotational movement in curved canals bends a file once per revolution, exposing the file to cyclic fatigue. More flexible files are less susceptible to cyclic fatigue and therefore less likely to break during a dental procedure. However, even superelastic files are not immune from cyclic fatigue.

To reduce a risk of file breakage, during the dental procedure, a set of NiTi files is typically used from relatively small to progressively larger sizes. To reduce a risk of file breakage, a file is advanced until a threshold resistance is encountered. The file is then withdrawn and a larger size file is introduced and advanced further apically. The procedure progresses sequentially until the canal is fully prepared.

After the canal has been shaped to a desired size and taper, gutta-percha or another suitable sealant is introduced into the prepared canal during a subsequent obturation phase of the dental procedure.

It would be desirable to provide an endodontic file that is even more resistant to torsional stress and cyclic fatigue when operating in the canal. It would be desirable to provide an endodontic file that balances superelasticity and shape memory properties for a specific function and/or size associated with the file.

BRIEF DESCRIPTION OF THE DRAWINGS

The objects and advantages of the disclosure will be apparent upon consideration of the following detailed description, taken in conjunction with the accompanying drawings in which:

FIG. 19 shows illustrative information in accordance with principles of the disclosure; and FIG. 20 shows illustrative information in accordance with principles of the disclosure.

DETAILED DESCRIPTION OF THE INVENTION

Figure 1:
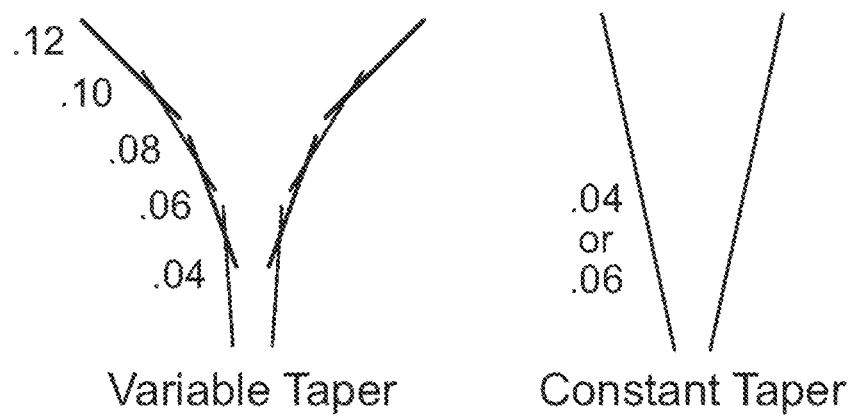
FIG. 1 shows illustrative apparatus and information in accordance with principles of the disclosure.

Preferred construction materials for endodontic files include stainless steel and NiTi alloys. Such materials, particularly NiTi alloys (e.g., copper nitinol, nickel nitinol, etc.), exhibit good flexibility, resilience and strength. NiTi files exhibit superelasticity and shape memory (or controlled memory) properties. Flexibility and strength reduce the likelihood of file breakage when operating in the canal.

Preferably, endodontic files utilized during a root canal procedure should be able to shape the canal in a manner that is suitable for obturation after the canal is shaped. Shaping the canal typically includes cutting dental tissue.

An endodontic file may be defined by one or more performance characteristics. One or more geometric parameters of a file affect a file's performance characteristic. A geometric parameter addresses single or a combination of performance characteristics. Illustrative geometric parameters include a file's volume, density, mass and/or cross-sectional surface area. Illustrative geometric parameters of illustrative files are shown below in Table 4.

TABLE 4

Illustrative geometric parameters

| Size | Density (milligrams per cubic inch) | Mass (milligrams) | Volume (milliliters) | Surface (square millimeters) |
|---|---|---|---|---|
| 04/20-21 mm | 1000.0000 | 9.3600 | 0.0100 | 52.5100 |
| 04/20-25 mm | 1000.0000 | 12.5087 | 0.0125 | 65.0859 |
| 04/20-31 mm | 1000.0000 | 17.2283 | 0.0172 | 83.9498 |
| 04/25-21 mm | 1000.0000 | 9.7289 | 0.0097 | 55.1718 |

TABLE 4-continued

Illustrative geometric parameters

| Size | Density (milligrams per cubic inch) | Mass (milligrams) | Volume (milliliters) | Surface (square millimeters) |
|---|---|---|---|---|
| 04/25-25 mm | 1000.0000 | 12.8753 | 0.0129 | 67.7477 |
| 04/25-31 mm | 1000.0000 | 17.5947 | 0.0176 | 86.6116 |
| 04/30-21 mm | 1000.0000 | 9.9341 | 0.0099 | 56.4592 |
| 04/30-25 mm | 1000.0000 | 13.0805 | 0.0131 | 69.0351 |
| 04/30-31 mm | 1000.0000 | 17.8002 | 0.0178 | 87.8990 |
| 04/35-21 mm | 1000.0000 | 10.1547 | 0.0102 | 57.9671 |
| 04/35-25 mm | 1000.0000 | 13.3012 | 0.0133 | 70.5430 |
| 04/35-31 mm | 1000.0000 | 18.0209 | 0.0180 | 89.4069 |
| 04/40-21 mm | 1000.0000 | 10.1464 | 0.0101 | 58.1623 |
| 04/40-25 mm | 1000.0000 | 13.2928 | 0.0133 | 70.7382 |
| 04/40-31 mm | 1000.0000 | 18.0124 | 0.0180 | 89.6021 |
| 04/45-21 mm | 1000.0000 | 10.8646 | 0.0109 | 61.2640 |
| 04/45-25 mm | 1000.0000 | 14.0111 | 0.0140 | 73.8402 |
| 04/45-31 mm | 1000.0000 | 18.7307 | 0.0187 | 92.7041 |
| 04/50-21 mm | 1000.0000 | 11.2245 | 0.0112 | 62.6178 |
| 04/50-25 mm | 1000.0000 | 14.3709 | 0.0144 | 75.1937 |
| 04/50-31 mm | 1000.0000 | 19.0907 | 0.0191 | 94.0576 |
| 04/55-21 mm | 1000.0000 | 11.4780 | 0.0115 | 63.7530 |
| 04/55-25 mm | 1000.0000 | 14.6244 | 0.0146 | 76.0146 |
| 04/55-31 mm | 1000.0000 | 19.3441 | 0.0193 | 95.1928 |
| 06/13-21 mm | 1000.0000 | 9.5971 | 0.0096 | 53.3360 |
| 06/13-25 mm | 1000.0000 | 12.7435 | 0.0127 | 65.9119 |
| 06/13-31 mm | 1000.0000 | 17.4631 | 0.0175 | 84.7758 |
| 06/18-21 mm | 1000.0000 | 9.8623 | 0.0099 | 54.9017 |
| 06/18-25 mm | 1000.0000 | 13.0087 | 0.0130 | 67.4777 |
| 06/18-31 mm | 1000.0000 | 17.7283 | 0.0177 | 86.3415 |
| 06/20-21 mm | 1000.0000 | 10.0448 | 0.0100 | 56.0707 |
| 06/20-25 mm | 1000.0000 | 13.1912 | 0.0132 | 68.6466 |
| 06/20-31 mm | 1000.0000 | 17.9108 | 0.0179 | 87.5105 |
| 06/25-21 mm | 1000.0000 | 10.0815 | 0.0101 | 56.7516 |
| 06/25-25 mm | 1000.0000 | 13.2277 | 0.0132 | 69.3275 |
| 06/25-31 mm | 1000.0000 | 17.9470 | 0.0179 | 88.1913 |
| 06/30-21 mm | 1000.0000 | 10.4033 | 0.0104 | 58.0854 |
| 06/30-25 mm | 1000.0000 | 13.5495 | 0.0135 | 70.6614 |
| 06/30-31 mm | 1000.0000 | 18.2687 | 0.0183 | 89.5252 |
| 06/35-21 mm | 1000.0000 | 10.1629 | 0.0102 | 57.7443 |
| 06/35-25 mm | 1000.0000 | 13.3093 | 0.0133 | 70.3202 |
| 06/35-31 mm | 1000.0000 | 18.0289 | 0.0180 | 89.1841 |
| 06/40-21 mm | 1000.0000 | 10.7297 | 0.0107 | 60.1980 |
| 06/40-25 mm | 1000.0000 | 13.8758 | 0.0139 | 72.7739 |
| 06/40-31 mm | 1000.0000 | 18.5950 | 0.0186 | 91.6328 |
| 06/45-21 mm | 1000.0000 | 10.6597 | 0.0107 | 60.3724 |
| 06/45-25 mm | 1000.0000 | 13.8061 | 0.0138 | 72.9484 |
| 06/45-31 mm | 1000.0000 | 18.5256 | 0.0185 | 91.8122 |
| 06/50-21 mm | 1000.0000 | 11.0624 | 0.0111 | 62.0274 |
| 06/50-25 mm | 1000.0000 | 14.2086 | 0.0142 | 74.6033 |
| 06/50-31 mm | 1000.0000 | 18.9279 | 0.0189 | 93.4672 |
| 06/55-21 mm | 1000.0000 | 11.0188 | 0.0110 | 62.3864 |
| 06/55-25 mm | 1000.0000 | 14.1652 | 0.0142 | 74.9623 |
| 06/55-311 mm | 1000.0000 | 18.8848 | 0.0189 | 93.8262 |
| 08/25-17 mm | 1000.0000 | 7.7916 | 0.0078 | 46.1372 |

Illustrative geometric parameters include a file's taper (which includes un-tapered files) and a file's tip size.

A geometric parameter affects one or more of a file's performance characteristics. For example, a performance characteristic includes a file's cutting efficiency. The cutting efficiency typically depends on two geometric parameters: a) the rake angle of its cutting edge(s) and b) debris removal capability.

The rake angle is the angle formed by an axis perpendicular to the surface of the material (e.g., tooth tissue) to be removed and the file cutting edge. The rake angle may be negative or positive.

Debris removal capability is quantified by a Removal Area Coefficient (RAC). The RAC may be defined as:

RAC=Circumscribed Area/Material Cross-section Area/No. of Cutting Edges

Figure 2:
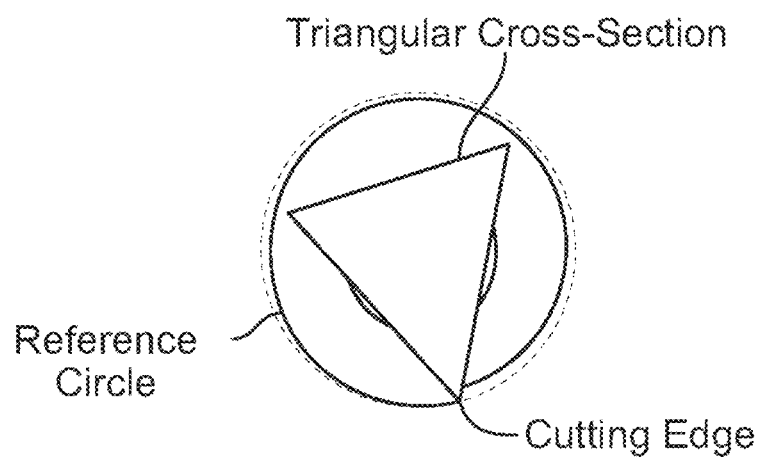
FIG. 2 shows illustrative apparatus and information in accordance with principles of the disclosure.

As shown in FIG. 2 (triangular cross-section configuration with three cutting edges), more cutting edges translate into lower RAC value.

Obtaining a preferable cutting efficiency of an endodontic file involves balancing the rake angle and RAC value. A high cutting capability (positive Rake Angle and/or multiple cutting edges) is typically incompatible with a low RAC value. For example, a file with a high cutting capability easily clogs during shaping of a canal. The clogging results from generating dentinal debris at a rate that is higher than the removal capability (e.g., a low RAC value). Clogging may lead to a jamming of the file, apical extrusion of the dentinal debris or even file breakage.

Existing endodontic files typically include two or more cutting edges. Multiple cutting edges reduce a file's RAC value.

A working length of a file has helical or non-helical flutes that include cutting edges. The working length is located between a proximal (shank) and distal (tip) end of a file. Endodontic files typically include two or more flutes. Generally, each flute has two cutting edges—a cutting edge and a trailing edge. A file having a triangular cross-section has three flutes and six theoretical edges. However, due to the triangular shape of the cross-section, the trailing edge of flute 1 is also the cutting edge of the flute 2, the trailing edge of the flute 2 is also the cutting edge of the flute 3, and the trailing edge of flute 3 is also the cutting edge of flute 1. Therefore, the triangular file typically has three cutting edges.

A geometric parameter of an endodontic file includes dimensions of the file's tip. The tip provides two main functions: a) the tip enlarges the canal during shaping and b) guides the file through the canal during shaping.

These two functions of the tip are accomplished by balancing various geometric parameters of the tip. Illustrative geometric parameters include the rake angle of the cutting edge, angle and radius of the tip's cutting edge and proximity of a flute end to the tip end of the file. Balancing such geometric parameters of endodontic files has not been easily achieved. For example, typically, in existing files, improved tip functionality may come at the expense of other performance characteristics of the file.

Flutes, taper, tip or any other geometric parameter of an endodontic files may be fabricated by twisting a file blank having a triangular, square, or rhomboid-shaped cross section. Another method for fabricating helical or non-helical flutes, taper, tip or other geometric parameters include a machining process. For example, a solid file blank is moved past a rotating grinding wheel. The file blank is repeatedly indexed and moved past the grinding wheel as many times as necessary to form a file having the desired geometric parameters.

Illustrative machining processes include using Electrical Discharge Machining (EDM) techniques. Illustrative EDM methods and apparatus are disclosed in U.S. Pat. No. 7,207,111, which is incorporated by reference herein in its entirety. Illustrative methods include using Electrochemical machining (ECM) techniques. Methods of manufacture include a combination of twisting and grinding.

In some embodiments, a file is manufactured by laser cutting a tube or grinding a tube. In some embodiments, a file is manufactured by twisting a flat sheet of material to form the cross section.

A performance characteristic of an endodontic file may be obtained by applying a heat treatment (hereinafter, "heat-treat"). A heat-treat is applied before and/or after fabricating a file's geometric parameters (e.g., flutes).

An illustrative heat-treat includes an annealing process. The annealing process is performed prior to forming a file blank, or performed on the blank after its formation. Annealing refers to heating an alloy to a threshold temperature and maintaining that temperature for a time sufficient to bring about a desired change in a property of the alloy.

For example, an annealing process for a NiTi file blank includes heating the blank at a threshold temperature and for a sufficient time to bring the blank to a state having a desired crystal structure between 100% austenite and 100% martensite. The crystal structure preferably includes a percentage of rhombohedral phase crystal structure. In some embodiments, the rhombohedral phase is the only crystal structure. Alternatively, the crystal structure is a combination of austenite and martensite without any rhombohedral phase.

A threshold temperature for inducing the desired crystalline structure may be dependent upon a particular NiTi alloy, but generally is in the range of about 250-700° C. for typical NiTi alloys, and is advantageously in the range of about 350-550° C. Generally, annealing time for a NiTi file blank ranges from about 15 seconds to about 20 minutes.

For example, a 1 mm diameter NiTi file blank may be annealed at a temperature about 495° C. for a period of 15 seconds to induce a crystal structure comprising 90%≤austenite<100%, the remainder being rhombohedral phase. Following an annealing process, a file blank may be cooled to room or ambient temperature, upon which it retains the desired crystal structure. After annealing, the instrument blank includes a superelastic material in a rhombohedral phase alone or in combination with austenite and/or martensite, or in a phase structure that is a combination of austenite and martensite.

After the annealing process, cutting edges are fabricated in the file blank. For example, the file blank may be twisted at low temperature (e.g., less than about 100° C.). The twisting may be performed at ambient temperature, without immersing the blank and tooling equipment into high temperature salt baths or exposing them to other high temperature methods.

After cutting edges are fabricated in the blank, a second heat-treat may be applied. Following the second heat-treat, the file may be cooled. For example, the filed may be rapidly quenched. The second heat-treat may be at a temperature in the range of about 300-800° C. The second heat-treat may be performed by a conventional heating oven, electrical heating, inductance heating or by submerging the twisted instrument in a heated liquid. The rapid quenching may immediately follow the second heat-treat. Rapid quenching cools the file within a fraction of a second to a few seconds.

Cooling may be performed by any suitable methods. For example, the heated file blanks may be cooled by placing the heated file blank in an environment at room temperature and waiting for the files to cool for a certain period of time.

The second heat-treat imbues the file with an austenitic finish temperature. The austenitic finish temperature is a temperature at about which NiTi exhibits superelastic properties. The second heat-treat may imbue the file with an austenitic finish temperature just below the temperature of a human body. When the austenitic finish temperature is just below the temperature of a human body, the file may exhibit superelasticity (typically increased rigidity or stiffness) when used in dental procedures performed within the mouth of a patient. In some embodiments, the first heat-treat (e.g., the annealing process) may also imbue the file with the austenitic finish temperature.

After quenching, a third heat-treat may be applied to relieve stress in the file. For example, to relieve stress within the file material, the file is heated to a temperature of about 150-300° C. An illustrative stress relieving heat-treat is performed for about 2-6 hours.

Illustrative heat-treat methods and apparatus are in U.S. Pat. No. 7,779,542, which is incorporated by reference herein in its entirety.

Even though file blanks are used to form files having different geometric parameter and/or performance characteristics, typically file blanks are heat-treated in a uniform fashion. The present disclosure relates to variable heat-treat methods that are applied to a file blank based on desired geometric parameters and associated performance characteristics expected to be fabricated in the blank. Preferably, the variable heat-treat is applied to a file blank before cutting edges are formed in the file. Embodiments also include applying a variable heat-treat to a file after cutting edges have been formed in the file.

When flutes are formed in the blank after application of the variable heat-treat, formation of the flutes imbues the file with a unique aesthetic color scheme. The color scheme improves the user experience and attractive appearance of the file. For example, by applying a variable heat-treat sequence before fluting, a body of the file retains a darker or matte look (e.g., dark blue/brown) and flutes appear shiny. Similarly, by applying a variable heat-treat sequence before grinding, the blank obtains a darker or matte look (e.g., dark blue/brown).

Figure 3:
FIG. 3 shows illustrative apparatus in accordance with principles of disclosure.
Figure 4:
FIG. 4 shows illustrative apparatus in accordance with principles of disclosure.

In some embodiments, depth markers ground into the file after application of a variable heat-treat sequence provide the markers with enhanced visibility. Exemplary depth markers may be ground at 16 mm from the file tip. Similarly, grind marks or grooves can be added to the files, such that the contrasting dark/shiny appearance will allow the grind marks or grooves to be easier to see and distinguish. Illustrative files having such an appearance and grind marks are shown in FIGS. 3-4.

Application of a variable heat-treat creates a NiTi file having a customized balance of superelasticity and controlled memory properties for the geometric parameters of the file. Files having pre-determined percentages of superelasticity and control memory exhibit higher resistance to cyclic fatigue and torsional stress when operating in the canal. Applying variable heat-treat to files of different geometric parameters and associated performance characteristics fabricates files that are less likely to fracture during clinical use and allows fewer files to be used to perform a root canal procedure.

Variable heat-treat techniques may be used to produce a file having any suitable percentage of superelasticity and/or control memory. Such percentages of superelasticity and control memory correspond to percentages of austenite, martensite and/or r-phase crystalline structure within the file. Such customized files eliminate the need to create a hybrid technique using multiple file systems, because each size file in a system is designed to optimize performance.

In a preferred embodiment, the percentage of superelasticity to control memory within a file decreases as file size increases. File size may be defined using nomenclature described in the family of International Organization for Standardization of Geneva, Switzerland ("ISO") 3630 standards, which is hereby incorporated by reference herein in its entirety.

For example, variable heat-treat techniques may be used to fabricate a file having a relatively small 20/0.04 size that is 90% superelastic (e.g., more rigid or stiff). As a further example, variable heat-treat techniques may produce a file relatively large 55/0.05 size that is 90% control memory (e.g., more flexible).

A larger size file that is 90% control memory is more flexible when operating in the canal. Typically, files are configured to operate in the canal such that the body temperature is high enough to activate the austenite crystal structure within the file. Stress during operation may transform the austenite structure into its more malleable martensite crystal structure. Thus, the greater percentage of martensite phase (e.g., control memory) in a file blank when operating in the canal corresponds to more flexibility when operating in the canal. For larger size files, the greater degree of flexibility reduces a likelihood of the file fracturing when operating in the canal.

For smaller size files, a larger percentage of austenite phase (e.g., superelasticity) when operating in the canal may be desirable. Smaller size files are typically inherently more flexible than larger size files. Smaller size files are less likely to fracture even if they were to have increased stiffness. Thus, a smaller percentage of martensite (e.g., control memory) and a greater percentage of superelasticity corresponds to more stiffness when operating in the canal. Smaller size files are also subject to less stress when operating in the canal. Less stress allows smaller files to maintain a greater percentage of austenite when operating in the canal. Thus, smaller files formed in blanks that are mostly superelastic retain their stiffness when operating in the canal at a temperature above the austenitic finish temperature. For smaller size files, the greater degree of stiffness reduces a likelihood that the file fractures when operating in the canal.

Figure 5:
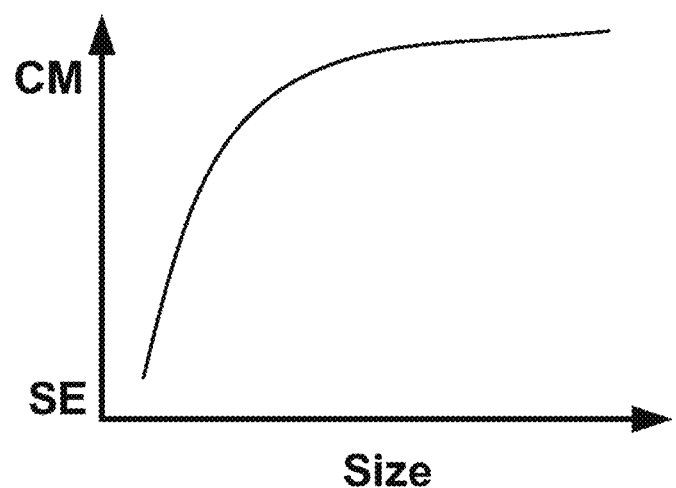
FIG. 5 shows illustrative information in accordance with principles of the disclosure.

FIG. 5 shows an illustrative and preferred relationship between varying percentages of superelasticity (SE), control memory (CM) and file size. Percentages of superelasticity and control memory within a file correspond to percentages of rhombohedral phase, austenite and/or martensite crystalline structure in the file.

Figure 6:
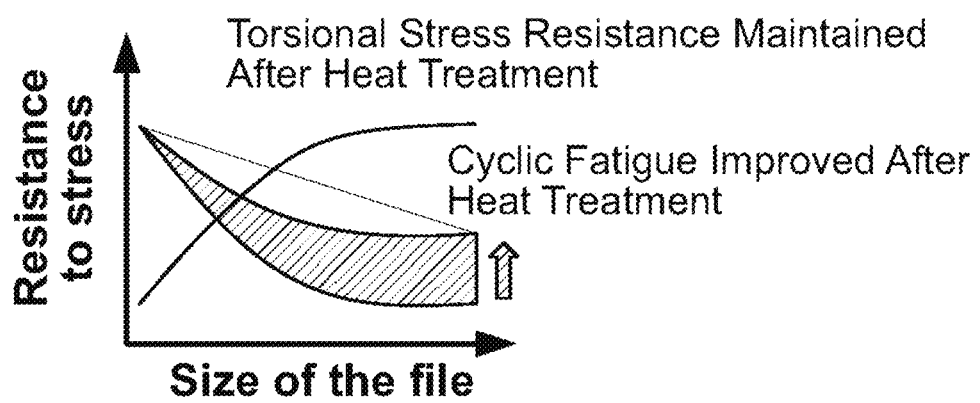
FIG. 6 shows illustrative information in accordance with principles of the disclosure.

Preferably, applying a variable heat-treat process to a file blank provides smaller size files that maintain resistance to torsional stress and provides larger size files with increased resistance to cyclic fatigue. FIG. 6 shows an illustrative and a preferred relationship between resistance to stress and file size. The shaded area (identified by the shaded arrow) shows improvement in resistance to cyclic fatigue as a result of applying a variable heat-treatment as opposed to conventional heat-treatments.

"Larger" and "smaller" size files may be defined based on one or more geometric parameters of a file. Such geometric parameters include any suitable parameters. Illustrative geometric parameters include file volume, mass and/or cross-sectional area of a file. Illustrative geometric parameters include files having a 02 taper, no taper, 04, 06, 08, 100 and/or 120 tapers. Illustrative geometric parameters include tip sizes from 06 to 100. A specific variable heat-treat is applied based on a specific set of geometric file parameters.

In a preferred embodiment, parameters (e.g., duration, temperature) of a variable-heat treat are determined based on a mass of a file. Mass of a file includes mass of a working length of the file. Mass includes the mass of a working length of the file and a length of the file that extends beyond the working length.

A variable-heat treat is typically applied to a file blank. Mass of a file may be determined based on an expected mass of the file after flutes or other geometric parameters are expected to be formed in the file blank. For example, a file blank may be ground such that the file includes a variable taper and/or a variable cross-section along its working length. The variable heat-treat applied to the file blank is determined based on an expected mass of the file after the geometric features are formed in the file blank.

In some embodiments, multiple variable heat-treats are applied to single file. For example, a file may be formed to include geometric parameters that vary along a length of the file. For example, a file blank may be formed (by grinding or twisting) to include variable tapers, variable helix angles variable flute depths or any other geometric parameter that varies along a length of a file. A different set of variable heat-treat parameters is applied to a length of a file blank based on geometric parameters expected to be applied along the length.

Figure 7:
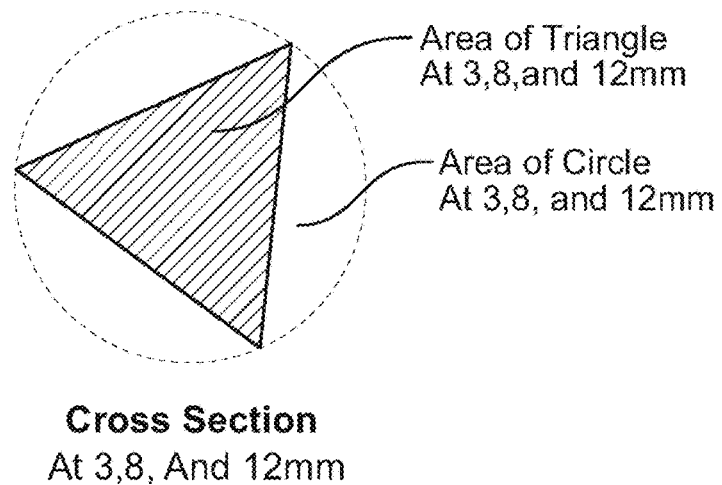
FIG. 7 shows illustrative apparatus and information in accordance with principles of the disclosure.
Figure 7:
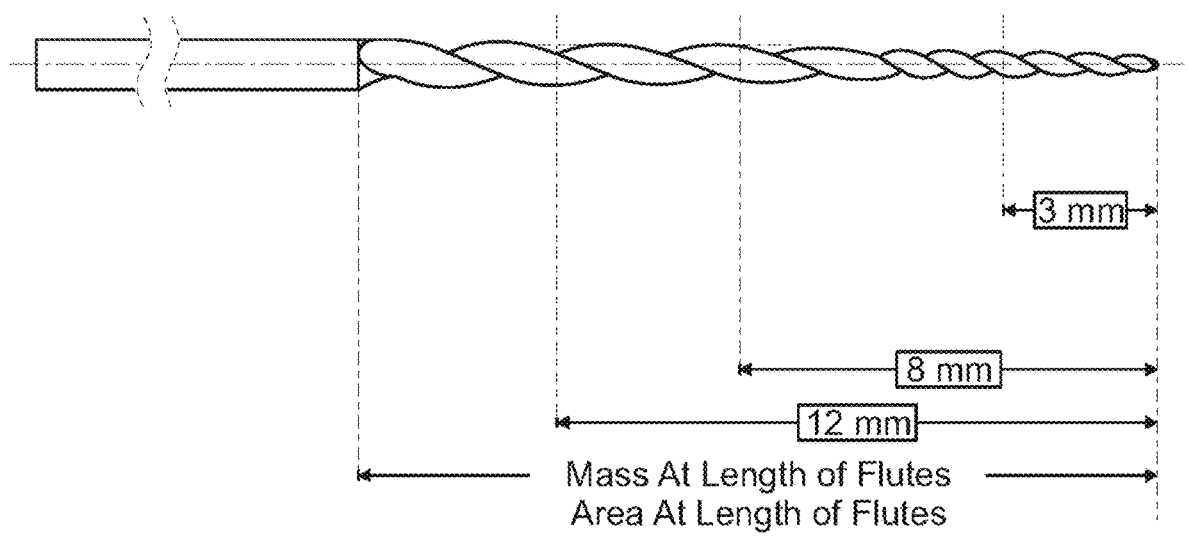

FIG. 7 shows an illustrative file (and an illustrative cross-sectional area of the file) that includes varied geometric parameters along its length.

The file shown in FIG. 7 includes a first section that extends from a tip of the file to 3 mm. The first section may have a first set of geometric parameters. The first section may have a first mass. In some embodiments, a first set of variable heat-treat parameters is applied to the first section based on the first mass. An illustrative set of variable heat-treat parameters includes heating temperature, heating time, cooling method and cooling time.

The file shown in FIG. 7 also includes a second section that extends from 3 mm from the tip to 8 mm from the tip. The second section may have a second set of geometric parameters and a second mass. The second mass may be different from the first mass. In some embodiments, a second set of variable heat-treat parameters is applied to the second section based on the second mass. The second set of heat-treat parameters may be different from the first set of variable heat-treat parameters.

The file shown in FIG. 7 also includes a third section that extends from 8 mm from the tip to 12 mm from the tip. The third section may have a third set of geometric parameters. The third section may have a third mass. The third mass may be different from the first mass and different from the second mass. In some embodiments, a third set of variable heat-treat parameters is applied to the third section based on the third mass. The third set of heat-treat parameters may be different from the first or second set of variable heat-treat parameters.

Illustrative geometric parameters and associated heat-treat values for the geometric parameters are shown below. Geometric parameters and associated variable heat-treat values shown below are illustrative. For example, values of degrees may be +/−5 degrees Celsius and values of time may be +/−3 minutes. Files having geometric parameters not shown below may be manufactured by applying variable heat-treat values that are between the variable heat-treat values shown below of the smallest and largest magnitude geometric parameters shown below. In some embodiments, variable heat-treat values are determined based on the proportion of shape memory to superelasticity desired.

Mass Properties of File Having Triangular Cross-Section, 04 Taper, 20 Tip and 12 mm Length:
    Density: 16387.06400000 milligrams per cubic inch
    Mass: 0.78008316 milligrams
    Volume: 0.00004760 cubic inches
    Surface area: 0.02090361 square inches
    Heating Temperature: 465° C.
    Heating Time: 5 minutes
    Cooling Method: Rapid Quench
    Cooling Time: <1.25 seconds Mass Properties of File Having Triangular Cross-Section, 06 Taper, 13 Tip and 12 mm Length:
    Density=16387.06400000 milligrams per cubic inch
    Mass=0.90491513 milligrams
    Volume=0.00005522 cubic inches
    Surface area=0.02185530 square inches
    Heating Temperature: 467° C.
    Heating Time: 7 minutes
    Cooling Method: Rapid Quench
    Cooling Time: <1.25 seconds Mass Properties of File Having Triangular Cross-Section, 06 Taper, 55 Tip and 12 mm Length:
    Density=16387.06400000 milligrams per cubic inch
    Mass=2.18778611 milligrams
    Volume=0.00013351 cubic inches
    Surface area=0.03640349 square inches
    Heating Temperature: 515° C.
    Heating Time: 180 minutes
    Cooling Method: Air cool to room temperature
    Cooling Time: 30-60 minutes Mass Properties of File Having Triangular Cross-Section, 08 Taper, 25 Tip and 12 mm Length:
    Density=16387.06400000 milligrams per cubic inch
    Mass=1.49426111 milligrams
    Volume=0.00009119 cubic inches
    Surface area=0.02879175 square inches
    Heating Temperature: 500° C.
    Heating Time: 180 minutes
    Cooling Method: Air cool to room temperature
    Cooling Time: 30-60 minutes Preferably, when operating in the canal, an endodontic file should preserve a natural curvature of the root canal. Preserving the natural curvature includes keeping the apical foramen as small as practical. A file should preferably shape a canal with no or minimal foramen transportation. A file should preferably shape the canal without perforating the canal.

Figure 8:
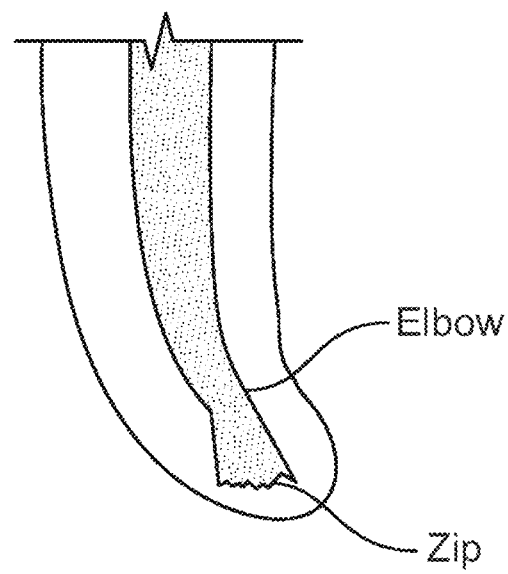
FIG. 8 shows illustrative anatomy.

To better quantify the effect of file transportation during root canal shaping, additional literature has been reviewed. As described by Dr. F. S. Weine on his scientific article: "The effect of preparation procedures on original canal shape and on apical foramen shape," the narrowest portion of the canal is not on the apex, but near the middle portion of the curve, called "elbow" (shown in FIG. 8).

Files fabricated using variable heat-treat exhibit enhanced performance characteristics. Typical files, when operating in the canal, tend to straighten within the canal. During insertion or withdrawal, a file may "ride" the inner portion of the canal between the elbow and the wall on the outer portion of the curve between the elbow and the apex. A file fabricated using variable-heat is less likely to have a tendency to straighten within the canal.

Figure 9:
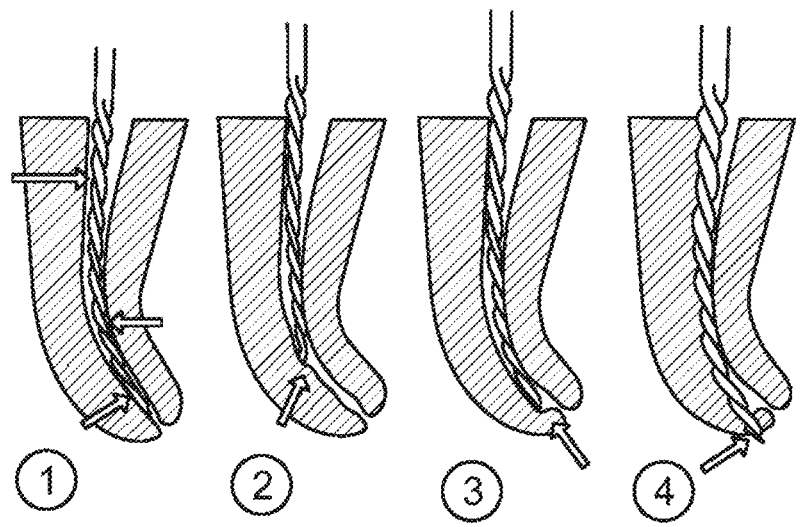
FIG. 9 shows illustrative apparatus and anatomy in accordance with principles of the disclosure.

A similar study has been conducted by Dr. P. J. Brockhurst, and described in the publication "Changes in root canal morphology in simulated curved canals." Based on Dr. Brockhurst's study, NiTi rotary files produce significant transportation of the canal on the convex side of the apex and on the concave side of the curved portion of the root canal, and the greatest transportation can be estimate at the apex and 2 mm from the apex. FIG. 9 shows examples of transportation and perforation. The arrows in FIG. 9 show points with the canal at which rotary files tend to alter a canal path. A file fabricated using variable-heat is less likely to "transport' and alter the canal path.

Due to a large variation in tooth anatomy, preserving the natural curvature of the root canal and avoiding the foramen transportation, a typical dental procedure involves use of two or more files to shape a canal or clean infected tissue out of the canal.

For example, when performing a procedure using NiTi files, a pilot glide path is initiated into the canal using K-files. After an initiating the glide path, one or more NiTi files are used to progressively shape the canal to a desired apical size and taper.

Utilizing variable heat-treat, an endodontic file is fabricated that balances superelasticity and/or control memory for use within a particular part of the tooth anatomy. For example, in some embodiments, a variable heat-treat provides larger size files with more control memory (and more flexibility when operating in the canal) than would have been providing when using uniformly applied heat-treat methods.

Using variable heat-treat, larger size files (which are typically used to shape a coronal region of the canal) are manufactured with relatively higher percentages of elasticity than typically found in such larger size files. The added percentage of control memory provides sufficient flexibility to navigate an "elbow" region of a canal with reduced transportation. Files manufactured with a "customized" balance of superelasticity and/or control memory further reduce a risk of foramen transportation. Smaller size files include higher percentages of superelasticity (and more stiffness when operating in the canal) to reduce a risk of file breakage.

A desired percentage of superelasticity and/or control memory is determined based on total material mass of a file. For example, a file having more mass includes relatively higher percentages of control memory. Larger files or files with a larger mass are less susceptible to cyclic fatigue than files of a relatively smaller mass.

In a preferred embodiment, higher percentages of control memory (e.g., more flexibility) are useful in larger files. However, files fabricated having any suitable ratio of control memory to superelasticity are contemplated. Larger files are less susceptible to cyclic failure as a result of their larger mass and associated strength. Higher percentages of control memory provide larger files with a higher degree of flexibility when operating in the canal. Higher percentages of superelasticity (e.g., more stiffness) are particularly useful in files having relatively smaller mass. Such files are typically more susceptible to cyclic failure because their smaller mass provides less strength. Higher percentages of superelasticity provide smaller files with greater strength when operating in the canal.

Variable heat-treat also fabricates files that penetrate deeper into the canal with a lower risk of fracturing. Such files allow clinicians to shape canals using fewer files.

Variable heat-treat also provides files having customized degrees of flexibility. Pre-shapes files allow a file to navigate an irregularly shaped canal path. A customized flexibility increases a file's flexibility and allows the file to be shaped by clinicians prior to inserting the file into the canal. A pre-shaped and/or more flexible file is less susceptible torsional stress and/or cyclic fatigue when operating in the canal. Furthermore, pre-shaped and/or more flexible file minimizes transportation of the canal.

Table 5 below lists exemplary variable heat-treat parameters for illustrative file geometric parameters/performance characteristics:

TABLE 5

| Tip | Taper | Heat Pre/Post Flute Forming | Heating Temperature (° C.) | Heating Time (minutes) | Cooling Method |
|---|---|---|---|---|---|
| 20 | .04 | Pre | 465 | 7 | Rapid Quench <1.25 secs |

TABLE 5-continued

| Tip | Taper | Heat Pre/Post Flute Forming | Heating Temperature (° C.) | Heating Time (minutes) | Cooling Method |
|---|---|---|---|---|---|
| 25 | .04 | Pre | 465 | 9 | Rapid Quench <1.25 secs |
| 30 | .04 | Pre | 465 | 9 | Rapid Quench <1.25 secs |
| 30 | .04 | Pre | 500 | 180 | 60 minutes air cool |
| 35 | .04 | Pre | 500 | 180 | 60 minutes air cool |
| 35 | .04 | Pre | 465 | 9 | Rapid Quench <1.25 secs |
| 40 | .04 | Pre | 500 | 190 | 60 minutes air cool |
| 45 | .04 | Pre | 505 | 195 | 60 minutes air cool |
| 50 | .04 | Pre | 507 | 195 | 60 minutes air cool |
| Fi50 | .04 | Pre | 507 | 195 | 60 minutes air cool |
| 55 | .04 | Pre | 510 | 200 | 60 minutes air cool |
| 25 | .08 | Pre | 465 | 10 | Rapid Quench <1.25 secs |

Based on customized flexibility provided by a variable heat-treat, endodontic files are manufactured having one or more performance characteristics that utilize the customized flexibility.

For example, a file may be formed with a variable taper core. A variable taper core refers to a cross sectional taper (as opposed to an outside taper of a file.) Preferably, varying cross-sections are formed by grinding a solid blank. A file may include a rectangular cross section near a tip and a triangular cross section along the working length's largest diameter (theoretically those cross sections have been shown to produce the lowest torsional stress at these points).

File cross sections vary differently or independently from an outer profile of the file. For example, a cross sectional taper may include any suitable number of tapers or non-tapered lengths. As a further example, a file may include two, three or six different tapers. Having different tapers allows for adjustment in file flexibility in targeted areas of the file and less flexibility in other areas of the file. Variable taper may be defined based on a variable distance from an inner vertex of the cross-section of the file to a center-line of the file.

Variable heat-treat techniques provide a variable taper file with a crystal structure that is best suited to the desired geometric parameters and/or desired performance characteristics of the file. Variable heat-treat imbue a file with specific percentages of superelasticity and shape memory based on an expected variable taper or other geometric parameter that will be fabricated in the file.

As a further example, a file includes various geometric parameters associated with its cutting edges. Files may include a variable pitch flute. A helix angle of a flute may be larger at a point along the file length that is closer to the file tip. An exemplary helix angle is 21° at the tip. An exemplary helix angle is 20° at about 3 mm from the tip. An exemplary helix angle is 17° at about 8 mm from the tip. A variable heat-treat improves overall file performance by providing a customized crystal structure that enhances efficiency of performance characteristics associated with the file's cutting edges.

Files include a variable flute diameter. A flute diameter may vary along a working length of the file. A file may include a maximum flute diameter. A maximum flute design reduces dentin removed from a coronal region of the tooth. Preferably, the maximum flute diameter design is minimally invasive, and it minimizes an amount of dentin removal in the canal's coronal ⅓, preserving more tooth structure than traditional continuously tapered and progressively tapered files.

Figure 10:
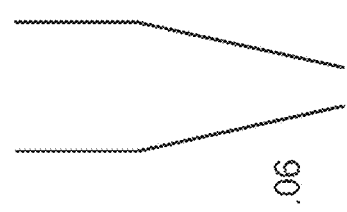
FIG. 10 shows illustrative apparatus and information in accordance with principles of the disclosure.
Figure 11:
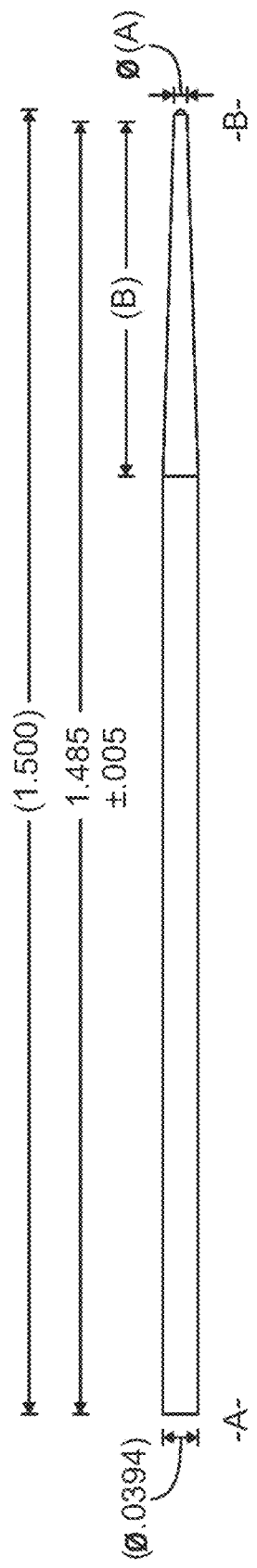
FIG. 11 shows illustrative apparatus and information in accordance with principles of the disclosure.

FIG. 10 shows an illustrative constant taper and a maximum flute design. FIG. 11 shows an illustrative file or file blank having a constant taper and a maximum flute diameter.

Files include a quantity of flutes for a given length. For example, a file may include a first number of flutes along a first length and a second number of flutes along a second length. Percentages of superelasticity and shape memory imbued in the file as a result of a variable heat-treat enhance performance characteristics associated with the quantity of flutes fabricated in a file.

A flute has a length. For example, flutes may be more tightly wound (e.g., shorter length) closer to a tip of the file compared to flutes further from the tip. Flutes further from the tip may be less tightly wound (e.g., longer length) than the flutes closer to the tip.

A flute has a depth. A depth of the flute may increase RAC of the file. A depth of the flute and give a file an "off-center" geometric property. A depth of the flute effects flexibility of the file. A flute may be helical, linear (horizontal or vertical) or have any suitable geometric shape. Percentages of superelasticity and shape memory imbued in the file as a result of a variable heat-treat enhance performance characteristics associated with a flute depth of geometric shape.

In some embodiments, a variable heat-treat is applied based on obtaining a desired performance characteristic in a cross-section of a file and/or blank. Variable heat-treat is preferably applied to file having a triangular cross section. Sides of the triangular cross section may have any suitable lengths. An exemplary cross section includes an equal-sided (equilateral) triangular cross section. Exemplary lengths of each side of the cross-section are 3, 8 or 12 millimeters ("mm").

A variable heat-treat may be applied to a file blank based on an expected tip size. For example, a file may include a "bullet" shaped tip design associated with a 45° angle and 0.003" radius. In some embodiments, a file tip looks like a spoon—half conical with a concave radius on it. Such a tip design results from a single flute design and associated cross sectional profiles.

Figure 12:
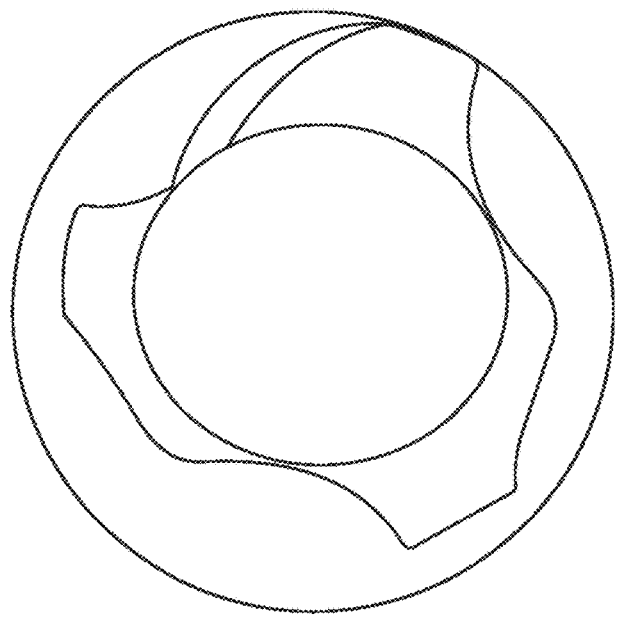
FIG. 12 shows illustrative apparatus in accordance with principles of the disclosure.
Figure 13:
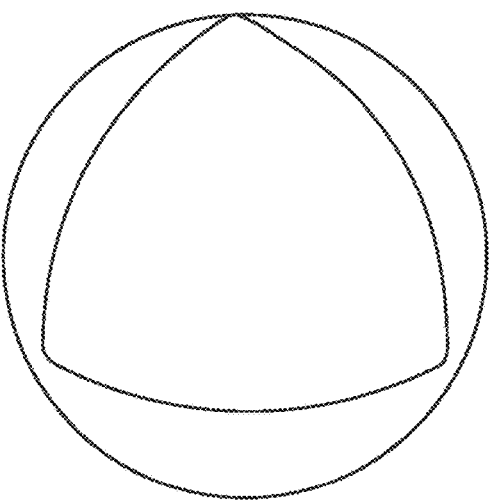
FIG. 13 shows illustrative apparatus in accordance with principles of the disclosure.
Figure 14:
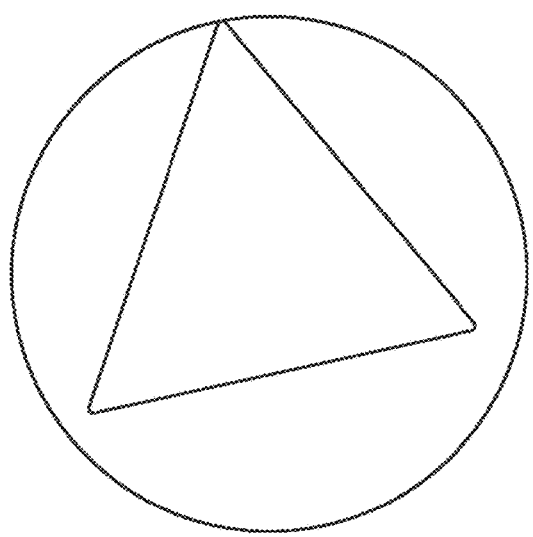
FIG. 14 shows illustrative apparatus in accordance with principles of the disclosure.
Figure 15:
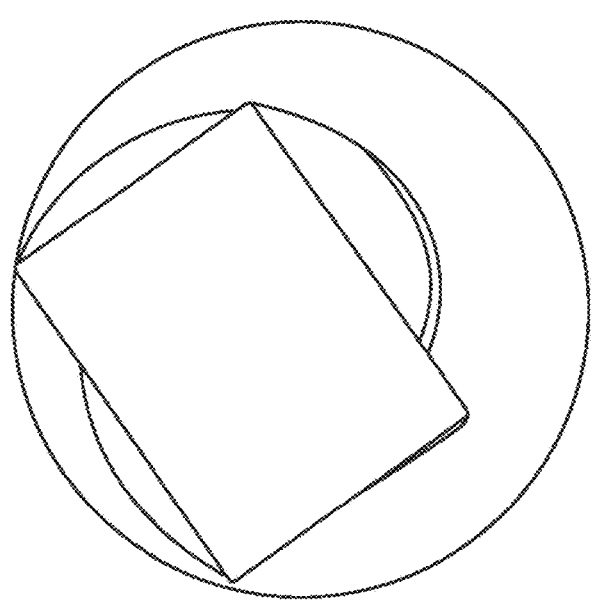
FIG. 15 shows illustrative apparatus in accordance with principles of the disclosure.

Files vary in cross-section. For example, FIG. 12 shows an illustrative cross-section that includes a landed design. FIG. 13 shows an illustrative cross-section that includes a non-landed design. FIG. 14 shows an illustrative cross-section that includes a triangular design. FIG. 15 shows an illustrative rectangular cross-section.

FIGS. 12-15 show illustrative cross sections include an offset design. In an offset design, two or more sides/blades do not make contact with the canal wall at the same diametrical point, at the same time. An off-center cross-section increases flexibility of the file. A cross-section may be convex or concave relative to a center of the cross-section.

A file may include a hollow area that extends through (centered or off-center) the file. The hollow area may be visible in a cross-sectional view of the file. The hollow area may extend along a full length or along a limited length of the file. The hollow area may extend along a length of a fluted end of the file. The hollow area may extend though a center of the file. The hollow area may be positioned off-center (relative to the longitudinal central axis of the file).

The hollow area facilitates removal of dentinal debris and necrotic tissue during the canal shaping process. For example, debris typically flows from an apical foramen of the tooth through the hollow area. Debris that flows through the hollow area exits the hollow area at or near a coronal area of the tooth. The hollow area also is utilized to channel gutta-percha or other sealants into the canal during obturating and sealing of the canal.

A variable heat-treat may be applied to the file based on expected cross-sectional design for the file.

Variable heat-treat may be applied to files based on an anticipated function of a file. For example, variable heat-treat is applied to the following illustrative files:

Orifice opener (25/08/17 mm);
Glide Path Files (13/06, 18/06, 21/25/31 mm length); and
Shaping Files (20-55 tip size, 04 and 06 taper, 21/25/31 mm length).

Figure 16:
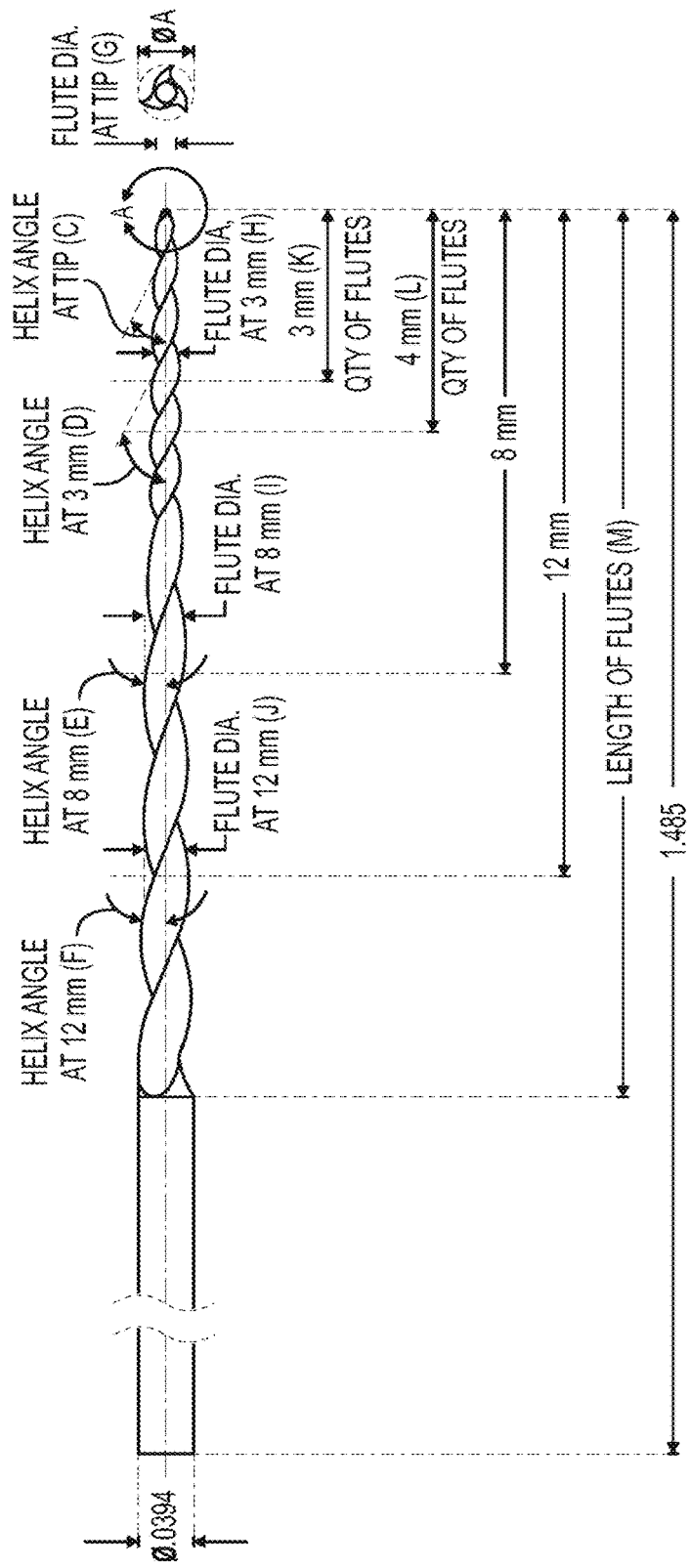
FIG. 16 shows illustrative apparatus and information in accordance with principles of the disclosure.
Figure 18:
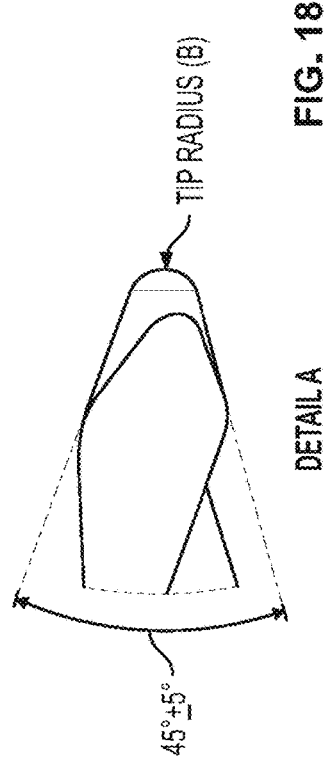
FIG. 18 shows illustrative apparatus and information in accordance with principles of the disclosure.
Figure 17:
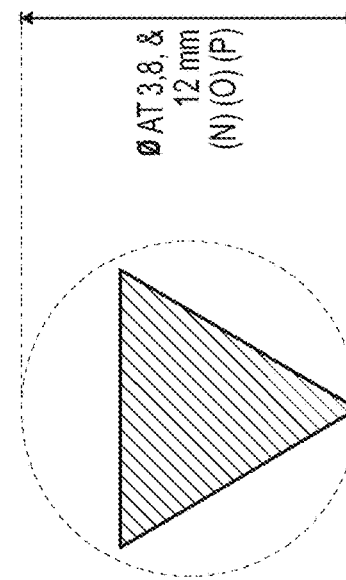
FIG. 17 shows illustrative apparatus and information in accordance with principles of the disclosure.

FIG. 16 shows an illustrative file and associated geometric parameters for an endodontic file manufactured using variable heat-treat. FIG. 17 shows an illustrative cross section, and associated geometric parameters, of the file shown in FIG. 16. FIG. 18 shows illustrative tip geometric parameters of the file shown in FIG. 16.

FIGS. 19 and 20 show illustrative sizes and associated geometric parameters of illustrative files manufactured using variable heat-treat.

Files manufactured using variable heat-treat may be provided to clinicians in pre-sterilized packaging. Pre-sterilized packaging eliminates a need to autoclave or otherwise sterilize a file prior to first use.

Thus, apparatus and methods for a variable heat-treat endodontic file have been provided. Persons skilled in the art will appreciate that the present disclosure can be practiced by other than the described examples, which are presented for purposes of illustration rather than of limitation.

What is claimed is:

1. A heat-treatment for a set of Nickel-Titanium (NiTi) endodontic files, wherein for each file in the set, a heat-treatment is applied to a file blank based on a mass of a file that will be fabricated using the file blank.

2. The heat-treatment of claim 1 wherein the heat treatment is applied to the file blank based on one or more geometric parameters that will be fabricated in the file blank, the one or more geometric parameters comprising:
  a) a volume of each file in the set;
  b) a cross-sectional area of each file in the set;
  c) a taper of each file in the set; or
  d) a tip size of each file in the set.

3. The heat-treatment of claim 1, wherein the heat-treatment customizes flexibility of each file in the set based on the mass.

4. The heat-treatment of claim 3 wherein at least one file in the set comprises a constant taper and a maximum flute diameter.

5. The heat-treatment of claim 3 wherein for each file in the set of files, the heat-treatment provides a threshold resistance of each file to torsional stress and cyclic fatigue.

6. The heat-treatment of claim 5 wherein the heat-treatment reduces a risk that any file in the set will fracture during operation.

7. A method for manufacturing an endodontic file, the method comprising applying a heat-treatment to a file blank based on a mass of the endodontic file that will be formed using the file blank after applying the heat-treatment to the file blank.

8. The method of claim 7 wherein the heat-treatment defines a percentage of superelasticity and a percentage of control memory in the endodontic file.

9. The method of claim 7 wherein, the heat-treatment provides the endodontic file with a threshold resistance to torsional stress.

10. The method of claim 7 wherein, the heat-treatment provides the endodontic file with a threshold resistance to cyclic fatigue.

\* \* \* \* \*